(12) United States Patent
Payne et al.

(10) Patent No.: US 10,327,868 B2
(45) Date of Patent: Jun. 25, 2019

(54) SELF LIGATING ORTHODONTIC BRACKET WITH COPLANAR SPRING

(71) Applicant: Ortho Organizers, Inc., Carlsbad, CA (US)

(72) Inventors: Mark A. Payne, Oceanside, CA (US); Colin Corey, Encinitas, CA (US)

(73) Assignee: Ortho Organizers, Inc., Carlsbad, CA (US)

( * ) Notice: Subject to any disclaimer, the term of this patent is extended or adjusted under 35 U.S.C. 154(b) by 251 days.

(21) Appl. No.: 15/267,611

(22) Filed: Sep. 16, 2016

(65) Prior Publication Data

US 2018/0078341 A1   Mar. 22, 2018

(51) Int. Cl.
*A61C 7/28* (2006.01)
*A61C 7/30* (2006.01)

(52) U.S. Cl.
CPC ............... *A61C 7/287* (2013.01); *A61C 7/30* (2013.01)

(58) Field of Classification Search
CPC .................................. A61C 7/287; A61C 7/30
USPC ........................................................ 433/8–15
See application file for complete search history.

(56) References Cited

U.S. PATENT DOCUMENTS

| | | | |
|---|---|---|---|
| 6,071,118 A | 6/2000 | Damon | |
| 6,071,119 A | 6/2000 | Christoff et al. | |
| 6,190,166 B1 * | 2/2001 | Sasakura | A61C 7/12 433/11 |
| 7,335,020 B2 | 2/2008 | Castner et al. | |
| 7,611,353 B2 | 11/2009 | Sommer | |
| 7,621,743 B2 | 11/2009 | Bathen et al. | |
| 7,704,072 B2 | 4/2010 | Damon | |
| 7,717,706 B2 | 5/2010 | Forster et al. | |
| 7,785,101 B2 | 8/2010 | Forster et al. | |
| 7,878,802 B2 | 2/2011 | Hagelganz et al. | |
| 7,963,767 B2 | 6/2011 | Lewis et al. | |
| 8,029,276 B1 | 10/2011 | Lokar | |
| 8,038,438 B2 | 10/2011 | Ruiz Diaz et al. | |
| 8,113,827 B2 | 2/2012 | Farzin-Nia et al. | |
| 8,246,348 B2 | 8/2012 | Heiser | |
| 8,246,349 B2 | 8/2012 | Scommegna et al. | |
| 8,297,970 B2 | 10/2012 | Kanomi et al. | |
| 8,414,292 B2 | 4/2013 | Lopes | |

(Continued)

OTHER PUBLICATIONS

International Search Report, dated Feb. 2, 2017, 5 pages, from PCT/US2016/059197.

(Continued)

*Primary Examiner* — Yogesh P Patel
(74) *Attorney, Agent, or Firm* — Fulwider Patton LLP

(57) ABSTRACT

An orthodontic self-ligating bracket for orthodontic treatment of maloccluded teeth is provided that includes a bracket body and a bracket door including a coplanar spring. The bracket body has a base that is contoured to attach to a surface of a tooth, a archwire slot on the top side of the bracket body extending in a mesiodistal direction and configured to releasably retain an archwire, and a bracket groove on the top side of the bracket body extending in an occlusogingival direction towards the archwire slot. The coplanar spring includes a spring body and one or more legs that deflect in direction generally coplanar with a plane of motion of the bracket door. The one or more legs interact with one or more depressions in the bracket body to move and retain the bracket door on the bracket body.

20 Claims, 1 Drawing Sheet

(56) References Cited

U.S. PATENT DOCUMENTS

| | | | |
|---|---|---|---|
| 8,568,139 | B2 | 10/2013 | Roncone |
| 8,585,398 | B2 | 11/2013 | Yeh et al. |
| 8,636,507 | B2 | 1/2014 | Voudouris |
| 8,932,053 | B2 | 1/2015 | Curiel et al. |
| 9,089,386 | B2 | 7/2015 | Hagelganz et al. |
| 2002/0110771 | A1 | 8/2002 | Abels et al. |
| 2004/0072117 | A1* | 4/2004 | Farzin-Nia ............... A61C 7/20 433/10 |
| 2005/0239012 | A1* | 10/2005 | Bathen ................... A61C 7/287 433/10 |
| 2006/0228662 | A1 | 10/2006 | Lokar et al. |
| 2011/0076633 | A1 | 3/2011 | Bryant et al. |
| 2011/0086323 | A1 | 4/2011 | Wessinger |
| 2014/0199648 | A1 | 7/2014 | Lopes |
| 2014/0212828 | A1 | 7/2014 | Falcone et al. |
| 2014/0272753 | A1 | 9/2014 | Sommer et al. |
| 2015/0216629 | A1 | 8/2015 | Voudouris |
| 2015/0342707 | A1 | 12/2015 | Fernandez San Pablo |

OTHER PUBLICATIONS

International Search Report and Written Opinion, dated Nov. 6, 2017, 7 pages, from PCT/US2017/050741.

* cited by examiner

SELF LIGATING ORTHODONTIC BRACKET WITH COPLANAR SPRING

BACKGROUND

The present invention relates generally to orthodontic brackets for providing orthodontic treatment of maloccluded teeth, and more specifically relates to a self-ligating orthodontic bracket with a sliding door including a coplanar spring for releasably retaining an archwire in an archwire slot.

Orthodontic brackets or braces are a very popular method of treating misaligned or maloccluded teeth. Traditionally, brackets are bonded to the labial or possibly lingual surfaces of a patient's teeth, and an archwire is placed in the slot of each bracket to guide movement of the teeth. Brackets are generally pre-adjusted to have built-in prescriptions of torque, tip, and in-out which are optimized for average cases of tooth movement. For instance, a bracket may be angled with respect to an occlusal plane (i.e. the bracket has a "tip angle"), depending on the tooth on which the bracket is to be placed. A ligature or ligating module, typically an elastomeric band such as a rubber band, is placed around the tie wings of a bracket to hold the archwire in place. However, ligatures typically cause friction on the wire during movement, resulting in a relatively slow treatment process, and they tend to attract plaque and trap food particles, a common cause of tooth decay or infection. As a result, the use of self-ligating orthodontic brackets has steadily become a prevalent alternative solution to malocclusion treatment.

A self-ligating orthodontic bracket does not require a ligature to hold the archwire in place. Rather, the self-ligating bracket typically uses a clip or slide which opens and closes to releasably retain the archwire in the archwire slot. Thus, friction on wire movement is reduced compared to conventional brackets, resulting in potentially faster treatment time. An example of a conventional self-ligating bracket includes a base for attachment to a tooth surface, an archwire slot sized for receiving an archwire, a channel formed upon the base and transversely oriented to the archwire slot, and a sliding member slidably retained in the channel and closeable over the archwire slot, where the sides of the bracket are crimped to securely retain the sliding member. Another type of self-ligating bracket includes a flexible pin to secure the sliding member in the closed position. However, these types of self-ligating brackets require additional processes or additives for securing the sliding member to the bracket, thus adding an additional layer of manufacturing complexity and increased cost.

Additionally, errors made while coining, bending, or crimping the sides of the bracket to retain the sliding member are typically irreversible without damaging the bracket, thus potentially resulting in significantly higher expenditures. For example, too much compression applied to the sides of the bracket may preclude the sliding member from moving, thus requiring the brackets to be discarded. Moreover, too little compression applied to the sides of the bracket may cause the sliding member to accidentally disengage from the bracket during use, resulting in patient and physician dissatisfaction and possible bracket recalls.

Hence, it is desirable to facilitate the assembly process by providing a self-ligating bracket that does not require crimping, bending, coining, fastening, or gluing to assemble or adhere the sliding member to the bracket. The present invention meets this and other needs.

SUMMARY OF THE INVENTION

The self-ligating orthodontic bracket according to the present invention provides one or more benefits and advantages not previously offered by the prior art, including but not limited to, a self-ligating bracket that does not require crimping, bending, coining, fastening, or gluing to assemble or adhere the sliding member or bracket door to the bracket. Accordingly, there is provided an orthodontic self-ligating bracket for orthodontic treatment of maloccluded teeth that includes a bracket body having a bottom side and a top side, and a bracket door including a coplanar spring slidably engaged with the bracket body. The bracket body includes a base on the bottom side of the bracket body that is contoured to attach to a surface of a tooth, an archwire slot on the top side of the bracket body extending in a mesiodistal direction and configured to releasably retain an archwire, and a bracket groove on the top side of the bracket body extending in an occlusogingival direction towards the archwire slot. The bracket door is slidably movable in the bracket groove along a plane of motion between an open position and a closed position. In the open position, the archwire slot is exposed to allow for placement and removal of the archwire. In the closed position, the archwire slot is enclosed to securely retain the archwire.

The coplanar spring includes a spring body and one or more legs connected to the spring body that deflect in a direction generally coplanar with the bracket door's plane of motion and that interact with one or more depressions or recesses in the bracket body. The one or more depressions interact with the coplanar spring to provide retaining forces on the bracket door, thereby preventing disassembly of the bracket door from the bracket body.

In a preferred embodiment, the coplanar spring includes a mesial leg and a distal leg. The mesial leg of the coplanar spring includes an outer mesial protrusion and an inner mesial protrusion, and the distal leg of the coplanar spring includes an outer distal protrusion and an inner distal protrusion. The mesial leg and the distal leg deflect in a direction generally coplanar with the plane of motion of the bracket door along the bracket groove. The bracket body includes an occlusal mesial depression or recess and an occlusal distal depression or recess that are occlusally located relative to the archwire slot, and a gingival mesial depression or recess and a gingival distal depression or recess that are gingivally located relative to the archwire slot. The occlusal mesial depression is preferably sized to receive the outer mesial protrusion of the coplanar spring, and the occlusal distal depression is preferably sized to receive the outer distal protrusion of the coplanar spring. Similarly, the gingival mesial depression is preferably sized to receive the inner mesial protrusion of the coplanar spring, and the gingival distal depression is preferably sized to receive the inner distal protrusion of the coplanar spring.

The bracket door is slidably movable into the open position upon application of a force to the door such that the outer mesial protrusion and the outer distal protrusion of the coplanar spring slide into the occlusal mesial protrusion and the occlusal distal protrusion of the bracket body, respectively. Similarly, the bracket door is slidably movable into the closed position upon application of a force to the door such that the inner mesial protrusion and the inner distal protrusion of the coplanar spring slide into the gingival mesial protrusion and the gingival distal protrusion of the bracket body, respectively.

In a preferred aspect, the self-ligating bracket includes an open force controlling member bounding the gingival mesial protrusion and the gingival distal protrusion that serves to provide opening forces on the bracket door. More particularly, the open force controlling member and gingival protrusions serve as retaining force generating features that retain the bracket door in the closed position using a biasing force and impose a requirement of a certain amount of force to be imposed on the coplanar spring before the bracket door can be opened. Moreover, the occlusal mesial depression and the occlusal distal depression further serve to provide retaining forces on the bracket door. More specifically, the occlusal depressions serve as retaining force generating features or indents that, upon interaction with the coplanar spring, provide retaining forces on the bracket door that retain the bracket door in the open position using a biasing force and prevent accidental disassembly of the bracket door from the bracket body.

The self-ligating bracket allows for ease of assembly of the bracket door to the bracket body yet relatively difficult disassembly. In particular, the bracket body includes tapered sides occlusally located relative to the bracket groove that engage and flex the one or more legs of the coplanar spring as the bracket door is being assembled onto the bracket body and that taper off towards the one or more depressions or recesses of the bracket body. In the preferred embodiment, the tapered sides taper off towards the occlusal mesial depression and the occlusal distal depression. When the bracket door is slidably moved along the bracket groove towards the archwire slot, the tapered sides cause the outer mesial protrusion and outer distal protrusion to deflect until the outer protrusions reach their respective occlusal depressions, after which the tension in the coplanar spring is allowed to release resulting in the bracket door being moved into the open position. Side walls of the occlusal depressions are cooperatively angled with respect to the outer protrusions of the coplanar spring to retain the coplanar spring in the bracket body, thus preventing the coplanar spring from being disassembled from the bracket body.

In a preferred aspect, the bracket door includes a coplanar spring that is integrally connected to, and inseparable from, the bracket door. Alternatively, the bracket door may include a door portion that is separate from the coplanar spring, where the door portion and coplanar spring are assembled together to create the bracket door. The self-ligating bracket with coplanar spring may be passive or active.

Other features and advantages of the present invention will become more apparent from the following detailed description of the preferred embodiments in conjunction with the accompanying drawings, which illustrate, by way of example, the operation of the invention.

DETAILED DESCRIPTION OF THE PREFERRED EMBODIMENTS

The present invention provides for a self-ligating orthodontic bracket that is easier to assemble and more cost-effective than conventional self-ligating orthodontic brackets. The present invention does not require crimping, bending, coining, fastening, gluing, or other similar methods of assembling or adhering a clip or slide to a bracket, but rather uses a coplanar spring to assemble the slide to the bracket.

Figure 1:
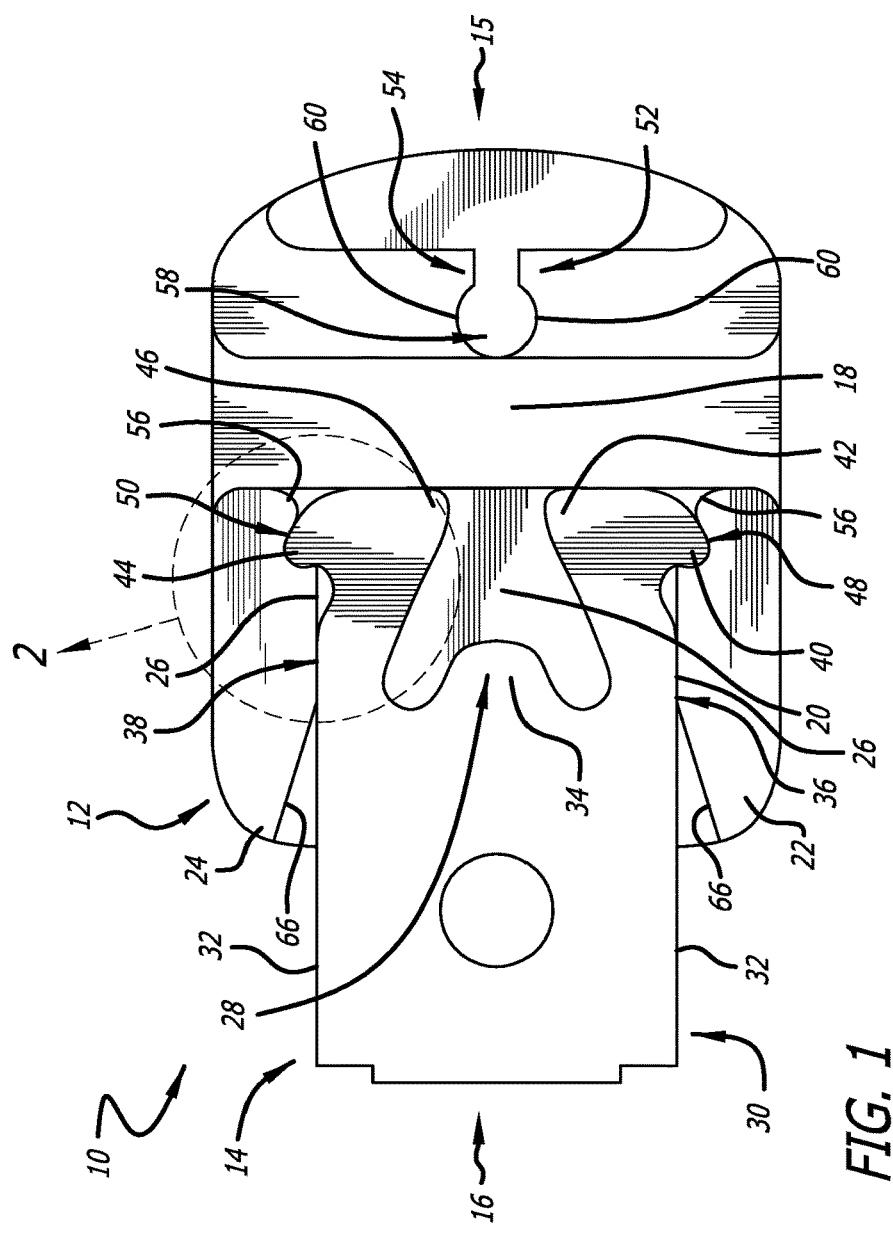
FIG. 1 is a top plan view of a self-ligating orthodontic bracket according to a preferred embodiment of the present invention including a bracket door with a coplanar spring.

FIG. 1 illustrates a preferred embodiment of a self-ligating orthodontic bracket where the spring mechanism is coplanar with the bracket door. In this embodiment, a self-ligating bracket 10 is provided including a bracket body 12 and a bracket door 14 that slidably engages with the bracket body. As illustrated in FIG. 1, the bracket body 12 includes a lingual side or bottom side, a gingival side 15, a labial side or top side, and an occlusal side 16. The bottom side of the bracket body has a base (not shown) which is compound contoured to engage a surface of a tooth, and an archwire slot or bracket slot 18 is positioned on the top side of the bracket body. The archwire slot extends in a mesio-distal direction and is sized to releasably retain an archwire. Preferably, the outside edges of the archwire slot are rounded to help prevent archwire notching during orthodontic treatment, thus reducing the risk of fray or damage caused by movement of the archwire within the archwire slot. Additionally, the self-ligating bracket may include curved tie wing grooves (not shown) underneath the tie wings on the occlusal side and the gingival side of the bracket body to allow for the use of optional ligatures or other elastomerics, such as steel ligatures or power chains, either individually or multiple simultaneously.

As illustrated in FIG. 1, the top side of the bracket body includes a bracket groove 20, a mesial surface 22, and a distal surface 24. The bracket groove extends in an occlusogingival direction and includes opposing side slots 26 which guide movement of the bracket door along the bracket groove. In one preferred aspect, the bracket groove ultimately connects with the archwire slot. Alternatively, a wall (not shown in the Figures) may separate the bracket groove from the archwire slot.

In this embodiment, the bracket door 14 includes a coplanar spring 28 that interacts with the bracket body 14, and a door portion 30 that slidably engages with the bracket groove 20. In the preferred embodiment depicted in FIG. 1, the coplanar spring 28 and door portion 30 are integrally connected to create a unitary bracket door 14. Alternatively, the coplanar spring 28 and door portion 30 may be separate components that when assembled together, create the bracket door 14. In a preferred aspect, the coplanar spring 28 is metal, and the door portion 30 and bracket body 12 are made of aesthetic material, for example, ceramic. Alternatively, the entire self-ligating bracket 10 may be completely metal, or completely made of aesthetic material such as ceramic or plastic. The door portion 30 includes opposing side edges 32 complementarily received by opposing side slots 26 of the bracket groove 20. The opposing side slots 26 guide and support the bracket door as the bracket door moves along a plane of motion away from and towards the archwire slot. The bracket body thus prevents the bracket door from moving along any other plane of motion, thereby preventing binding and reducing stress risers when the bracket door undergoes stress from the archwire.

The coplanar spring includes a spring body 34 preferably having a mesial leg 36 and a distal leg 38. The mesial leg includes an outer mesial protrusion 40 and an inner mesial protrusion 42, and the distal leg includes an outer distal protrusion 44 and an inner distal protrusion 46. Preferably, the mesial leg and the distal leg of the coplanar spring deflect, either elastically or plastically, in a direction generally coplanar with the plane of motion of the bracket door.

The bracket body 12 includes a plurality of depressions or recesses sized to receive or engage the outer and inner protrusions of the coplanar spring. Preferably, the bracket body includes an occlusal mesial depression or recess 48 that is sized to receive the outer mesial protrusion 40 of the mesial leg of the coplanar spring, and an occlusal distal depression or recess 50 that is sized to receive the outer distal protrusion 44 of the distal leg of the coplanar spring. Additionally, the bracket body preferably includes a gingival mesial depression or recess 52 that is sized to receive the inner mesial protrusion 42 of the mesial leg of the coplanar spring, and a gingival distal depression or recess 54 that is sized to receive the inner distal protrusion 46 of the distal leg of the coplanar spring.

The depressions are sized to engage the inner and outer protrusions of the coplanar spring such that the bracket door 14 can alternate or switch between an open position, in which the archwire slot 18 is exposed such that a user can remove or place an archwire, and a closed position, in which the archwire slot is enclosed such that the archwire is securely retained in the archwire slot. The bracket door is slidably movable into the open position upon application of a force to the door such that the outer mesial protrusion 40 and the outer distal protrusion 44 of the coplanar spring slide into the occlusal mesial depression 48 and the occlusal distal depression 50, respectively. Similarly, the bracket door is slidably movable into the closed position upon application of a force to the door such that the inner mesial protrusion 42 and the inner distal protrusion 46 of the coplanar spring slide into the gingival mesial depression 52 and the gingival distal depression 54, respectively.

The bracket body may include points or tapered angles 56 positioned adjacent to both occlusal depressions 48 and 50. These points define the location where the bracket door smoothly transitions to the open position. Moreover, the bracket body 12 includes an open force controlling member 58 that bounds gingival depressions 52 and 54. The open force controlling member is preferably circularly or "lollipop" shaped and include radial points 60 that define the point of transition where the bracket door smoothly transitions to the closed position. In a preferred aspect, the open force controlling member 58 is preferably exposed on the labial side of the bracket body for lower profile and easier moldability.

In one aspect, the bracket door includes an intermediate position between the open and closed positions that is located between the above-described points of transition (56 and 60). In the intermediate position, the bracket door must be physically moved towards the points of transition before the bracket door can slide into either the open or closed position. Thus, application of force is required to move the bracket door through the intermediate position before the bracket door can slide into either the open or closed position.

Figure 2:
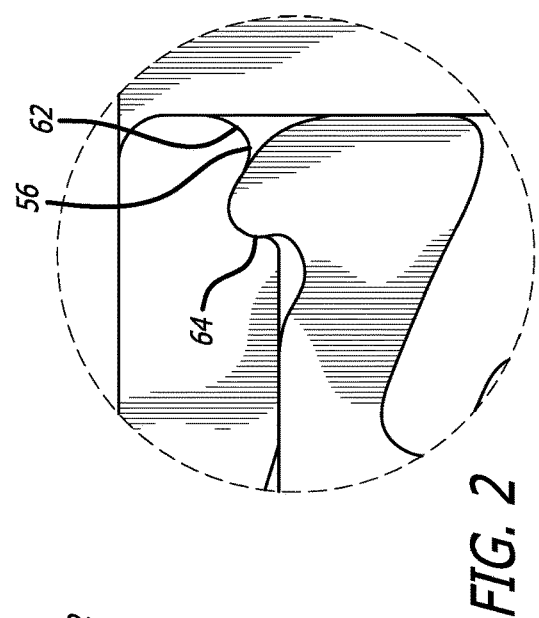
FIG. 2 is an enlarged view of the encircled portion in FIG. 1 depicting one of the "stay open" retaining features that retain the bracket door in the open position and prevent disassembly of the bracket door from the bracket body.

In a preferred aspect, the occlusal depressions serve to provide retaining or "stay open" forces on the bracket door. As shown in FIG. 2, as the bracket door is being moved along the bracket groove towards the open position from the intermediate position, the outer protrusions 40 and 44 of the coplanar spring engage tapered sides 62 on both the mesial and distal sides of the bracket body. The tapered sides 62 cause the outer protrusions to elastically or plastically deflect in a direction generally coplanar with the plane of motion of the bracket door until the outer protrusions reach tapered angles 56, after which the tension caused by the deflection of the outer protrusions is allowed to release, thus enabling the bracket door to be moved along the bracket groove to the open position through movement of the outer protrusions of the coplanar spring into respective occlusal depressions 48 and 50. Moreover, the occlusal depressions include side walls 64 on the mesial and distal sides of the bracket body that are cooperatively angled with respect to the outer protrusions to prevent the outer protrusions from moving any further in the occlusal direction. In this way, occlusal depressions 48 and 50 serve as retaining force generating features or "stay open" features that, upon interaction with the coplanar spring, provide retaining forces on the bracket door that retain or bias the bracket door in the open position and prevent accidental disassembly of the bracket door from the bracket body.

Similarly, as the bracket door is being moved along the bracket groove towards the closed position from the intermediate position, the inner protrusions 42 and 46 of the coplanar spring elastically or plastically deflect in a direction generally coplanar with the plane of motion of the bracket door as the inner protrusions move toward radial points 60 of the open force controlling member 58. Once the inner protrusions of the coplanar spring reach their respective radial points, the tension caused by the deflection of the inner protrusions is allowed to release, thus enabling the bracket door to be moved along the bracket groove to the closed position through movement of the inner protrusions of the coplanar spring into respective gingival depressions 52 and 54.

In another preferred aspect, the open force controlling member, in combination with the gingival depressions, serve to provide opening or "open" forces on the bracket door. When attempting to move the bracket door back towards the open position from the closed position, the open force controlling member provides a force on the coplanar spring as the inner protrusions move from the gingival depressions back toward radial points 60. Once the inner protrusions reach radial points 60, the coplanar spring is allowed to release its spring tension and the bracket door can be moved to the open position. In this way, open force controlling member 58 serves as a retaining force generating feature that not only serves to retain or bias the bracket door in the closed position, but also imposes a requirement of a certain amount of force to be imposed on the coplanar spring before the bracket door can be opened.

In one aspect, the self-ligating orthodontic bracket 10 may be preassembled with the bracket door 14 operatively engaged to the bracket body 12. Alternatively, the bracket door may be a separate component, in which case the bracket door can be easily assembled as subsequently described to engage with the bracket body. The bracket body 12 includes tapered sides 66 positioned on both the mesial side and distal side of the bracket body which taper towards the bracket groove 20. These tapered sides engage and flex the outer protrusions of the coplanar spring as the bracket door is slidably pushed towards the occlusal mesial depression 48 and the occlusal distal depression 50, allowing for easy assembly of the bracket door to the bracket body without the need for adhesives or additives. Moreover, as shown in FIG. 2, occlusal depressions 48 and 50 each include side walls 64 that are preferably, cooperatively angled to retain the coplanar spring on the bracket body and prevent accidental disassembly of the bracket door from the bracket body. The self-ligating bracket 10 therefore allows for ease of assembly while preventing disassembly without requiring crimping, bending, coining, fastening, gluing, or other similar assembly methods which were conventionally used in prior self-ligating brackets.

Various modifications within the scope of the preferred embodiments are possible. For example, although the coplanar spring described above is shown as having a two legs (the mesial leg and the distal leg), each having two protrusions (the occlusal protrusions and the gingival protrusions), a coplanar spring having a single leg with a single protrusion is also suitable. Thus, the coplanar spring may have just a mesial leg with only an occlusal mesial protrusion, or it may have just a distal leg with only an occlusal distal protrusion, for retaining the bracket door in the open position as described above. In another example, the self-ligating bracket 10 may be passive or active, the active version of which includes an additional active spring for contacting the archwire that may be inserted and retained in, or alternatively integral to and extending from, the spring body of the coplanar spring.

While certain embodiments have been illustrated and described herein, those embodiments are not necessarily to be construed as advantageous over other embodiments for implementing the apparatus of the present subject matter. Other variations and equivalents are possible and should be considered within the scope of the present subject matter.

What is claimed is:

1. An orthodontic self-ligating bracket for orthodontic treatment of maloccluded teeth, the bracket comprising:
    a bracket body having a lingual side, a labial side, a mesial side, and a distal side, the bracket body including
    a base on the lingual side of the bracket body that is contoured to attach to a surface of a tooth;
    an archwire slot on the labial side of the bracket body, the archwire slot extending in a mesiodistal direction and configured to releasably retain an archwire; and
    a bracket groove on the labial side of the bracket body, the bracket groove extending in an occlusogingival direction towards the archwire slot;
    a bracket door that slidably engages the bracket groove along a plane of motion between an open position and a closed position, wherein the archwire slot is exposed when the bracket door is in the open position to allow for placement and removal of the archwire, and wherein the archwire slot is enclosed to securely retain the archwire when the bracket door is in the closed position;
    wherein the bracket door includes a coplanar spring, the coplanar spring including a spring body, a mesial leg connected to the spring body and a distal leg connected to the spring body, wherein the mesial leg includes an outer mesial protrusion and an inner mesial protrusion, wherein the distal leg includes an outer distal protrusion and an inner distal protrusion; and wherein the mesial leg and the distal leg deflect in a direction generally coplanar with the plane of motion of the bracket door and interact with the bracket body; and
    wherein the bracket body includes one or more occlusal depressions that interact with the coplanar spring and provide retaining forces on the bracket door, thereby preventing disassembly of the bracket door from the bracket body.

2. The orthodontic self-ligating bracket of claim 1,
    wherein the one or more occlusal depressions include an occlusal mesial depression and an occlusal distal depression, wherein the bracket body further includes a gingival mesial depression and a gingival distal depression, wherein the occlusal mesial depression is sized to receive the outer mesial protrusion of the coplanar spring, wherein the occlusal distal depression is sized to receive the outer distal protrusion of the coplanar spring, wherein the gingival mesial depression is sized to receive the inner mesial protrusion of the coplanar spring, and wherein the gingival distal depression is sized to receive the inner distal protrusion of the coplanar spring; and
    wherein the bracket door is slidably movable into the open position upon application of a force to the door such that the outer mesial protrusion and the outer distal protrusion of the coplanar spring slide into the occlusal mesial protrusion and the occlusal distal protrusion of the bracket body, respectively, and wherein the bracket door is slidably movable into the closed position upon application of a force to the door such that the inner mesial protrusion and the inner distal protrusion of the coplanar spring slide into the gingival mesial protrusion and the gingival distal protrusion of the bracket body, respectively.

3. The orthodontic self-ligating bracket of claim 2, wherein the occlusal mesial depression and the occlusal distal depression each include a side wall that respectively retains the outer mesial protrusion and the outer distal protrusion of the coplanar spring when the bracket door is in the open position, thereby preventing disassembly of the bracket door from the bracket body.

4. The orthodontic self-ligating bracket of claim 2,
    wherein the bracket body includes tapered angles adjacent to the occlusal mesial depression and the occlusal distal depression that define the location where the bracket door moves into the open position;
    wherein the bracket body includes an open force controlling member bounding the gingival mesial depression and the gingival distal depression that includes radial points defining the location where the bracket door moves into the closed position; and
    wherein the bracket door slidably moves along the bracket groove between the open position and the closed position through an intermediate position located between the tapered angles and the radial points.

5. The orthodontic self-ligating bracket of claim 2, wherein the bracket body includes tapered sides occlusally located with respect to the bracket body that engage and flex the outer mesial protrusion and the outer distal protrusion of the coplanar spring as the bracket door is slidably moved along the bracket groove towards the occlusal mesial depression and the occlusal distal depression during assembly of the bracket door to the bracket body.

6. The orthodontic self-ligating bracket of claim 1, wherein the bracket door is preassembled on the bracket body by one of the manufacturer or end user of the orthodontic self-ligating bracket.

7. The orthodontic self-ligating bracket of claim 1, wherein the bracket door further includes a door portion separate from the coplanar spring, and wherein the door portion slidably engages with the bracket groove.

8. The orthodontic self-ligating bracket of claim 7, wherein the coplanar spring is metal, and wherein the door portion and the bracket body are ceramic.

9. The orthodontic self-ligating bracket of claim 7, wherein the coplanar spring is metal, and wherein the door portion and the bracket body are plastic.

10. The orthodontic self-ligating bracket of claim 7, wherein the door portion of the bracket door includes a door base having opposing side edges, and wherein the bracket groove includes opposing side slots complementarily sized to receive the door base of the door portion.

11. An orthodontic self-ligating bracket for orthodontic treatment of maloccluded teeth, the bracket comprising:
    a bracket body having a lingual side, a labial side, a mesial side, and a distal side, the bracket body including
    a base on the lingual side of the bracket body that is contoured to attach to a surface of a tooth;
    an archwire slot on the labial side of the bracket body, the archwire slot extending in a mesiodistal direction and configured to releasably retain an archwire; and a bracket groove on the labial side of the bracket body, the bracket groove extending in an occlusogingival direction towards the archwire slot;

a bracket door that slidably engages the bracket groove along a plane of motion between an open position and a closed position, wherein the archwire slot is exposed when the bracket door is in the open position to allow for placement and removal of the archwire, and wherein the archwire slot is enclosed to securely retain the archwire when the bracket door is in the closed position;

wherein the bracket door includes a coplanar spring, the coplanar spring including a spring body and one or more legs connected to the spring body, wherein the one or more legs deflect in a direction generally coplanar with the plane of motion of the bracket door and interact with the bracket body, wherein the one or more legs of the coplanar spring include a mesial leg connected to the spring body and a distal leg connected to the spring body, wherein the mesial leg includes an outer mesial protrusion and an inner mesial protrusion, wherein the distal leg includes an outer distal protrusion and an inner distal protrusion; and wherein the mesial leg and the distal leg deflect in a direction generally coplanar with the plane of motion of the bracket door;

wherein the bracket body includes an occlusal mesial depression, an occlusal distal depression, a gingival mesial depression, and a gingival distal depression, wherein the occlusal mesial depression is sized to receive the outer mesial protrusion of the coplanar spring, wherein the occlusal distal depression is sized to receive the outer distal protrusion of the coplanar spring, wherein the gingival mesial depression is sized to receive the inner mesial protrusion of the coplanar spring, and wherein the gingival distal depression is sized to receive the inner distal protrusion of the coplanar spring;

wherein the bracket door is slidably movable into the open position upon application of a force to the door such that the outer mesial protrusion and the outer distal protrusion of the coplanar spring slide into the occlusal mesial protrusion and the occlusal distal protrusion of the bracket body, respectively, and wherein the bracket door is slidably movable into the closed position upon application of a force to the door such that the inner mesial protrusion and the inner distal protrusion of the coplanar spring slide into the gingival mesial protrusion and the gingival distal protrusion of the bracket body, respectively; and wherein the occlusal mesial depression and the occlusal distal depression provide retaining forces on the bracket door when in the open position, thereby preventing disassembly of the bracket door from the bracket body.

12. The orthodontic self-ligating bracket of claim 11, wherein the occlusal mesial depression and the occlusal distal depression each include a side wall that respectively retains the outer mesial protrusion and the outer distal protrusion of the coplanar spring when the bracket door is in the open position, thereby preventing disassembly of the bracket door from the bracket body.

13. The orthodontic self-ligating bracket of claim 11, wherein the bracket body includes tapered angles adjacent to the occlusal mesial depression and the occlusal distal depression that define the location where the bracket door moves into the open position;

wherein the bracket body includes an open force controlling member bounding the gingival mesial depression and the gingival distal depression that includes radial points defining the location where the bracket door moves into the closed position; and wherein the bracket door slidably moves along the bracket groove between the open position and the closed position through an intermediate position located between the tapered angles and the radial points.

14. The orthodontic self-ligating bracket of claim 11, wherein the bracket body includes tapered sides occlusally located with respect to the bracket body that engage and flex the outer mesial protrusion and the outer distal protrusion of the coplanar spring as the bracket door is slidably moved along the bracket groove towards the occlusal mesial depression and the occlusal distal depression during assembly of the bracket door to the bracket body.

15. The orthodontic self-ligating bracket of claim 11, wherein the bracket door is preassembled on the bracket body by one of the manufacturer or end user of the orthodontic self-ligating bracket.

16. The orthodontic self-ligating bracket of claim 11, wherein the bracket door further includes a door portion separate from the coplanar spring, and wherein the door portion slidably engages with the bracket groove.

17. The orthodontic self-ligating bracket of claim 16, wherein the coplanar spring is metal, and wherein the door portion and the bracket body are ceramic.

18. The orthodontic self-ligating bracket of claim 16, wherein the coplanar spring is metal, and wherein the door portion and the bracket body are plastic.

19. The orthodontic self-ligating bracket of claim 16, wherein the door portion of the bracket door includes a door base having opposing side edges, and wherein the bracket groove includes opposing side slots complementarily sized to receive the door base of the door portion.

20. An orthodontic self-ligating bracket for orthodontic treatment of maloccluded teeth, the bracket comprising:

a bracket body having a lingual side, a labial side, a mesial side, and a distal side, the bracket body including a base on the lingual side of the bracket body that is contoured to attach to a surface of a tooth;

an archwire slot on the labial side of the bracket body, the archwire slot extending in a mesiodistal direction and configured to releasably retain an archwire; and a bracket groove on the labial side of the bracket body, the bracket groove extending in an occlusogingival direction towards the archwire slot;

a bracket door that slidably engages the bracket groove along a plane of motion between an open position and a closed position, wherein the archwire slot is exposed when the bracket door is in the open position to allow for placement and removal of the archwire, and wherein the archwire slot is enclosed to securely retain the archwire when the bracket door is in the closed position;

wherein the bracket door includes a coplanar spring, the coplanar spring including a spring body and one or more legs connected to the spring body, wherein the one or more legs deflect in a direction generally coplanar with the plane of motion of the bracket door and interact with the bracket body, wherein the one or more legs of the coplanar spring include a mesial leg connected to the spring body and a distal leg connected to the spring body, wherein the mesial leg includes an outer mesial protrusion and an inner mesial protrusion, wherein the distal leg includes an outer distal protrusion and an inner distal protrusion; and wherein the mesial leg and the distal leg deflect in a direction generally coplanar with the plane of motion of the bracket door;

wherein the bracket body includes an occlusal mesial depression, an occlusal distal depression, a gingival mesial depression, and a gingival distal depression, wherein the occlusal mesial depression is sized to receive the outer mesial protrusion of the coplanar spring, wherein the occlusal distal depression is sized to receive the outer distal protrusion of the coplanar spring, wherein the gingival mesial depression is sized to receive the inner mesial protrusion of the coplanar spring, and wherein the gingival distal depression is sized to receive the inner distal protrusion of the coplanar spring;

wherein the bracket door is slidably movable into the open position upon application of a force to the door such that the outer mesial protrusion and the outer distal protrusion of the coplanar spring slide into the occlusal mesial protrusion and the occlusal distal protrusion of the bracket body, respectively, and wherein the bracket door is slidably movable into the closed position upon application of a force to the door such that the inner mesial protrusion and the inner distal protrusion of the coplanar spring slide into the gingival mesial protrusion and the gingival distal protrusion of the bracket body, respectively; and wherein the occlusal mesial depression and the occlusal distal depression each include a side wall that respectively retains the outer mesial protrusion and the outer distal protrusion of the coplanar spring when the bracket door is in the open position, thereby preventing disassembly of the bracket door from the bracket body.

* * * * *